(12) United States Patent
Breeden et al.

(10) Patent No.: US 9,095,480 B2
(45) Date of Patent: Aug. 4, 2015

(54) REAR FASTENING ABSORBENT GARMENT

(71) Applicants: Catherine Kimrey Breeden, Wilmington, NC (US); Janice Kimrey Anderson, Kure Beach, NC (US); Debra Kimrey Bowers, Albermarle, NC (US)

(72) Inventors: Catherine Kimrey Breeden, Wilmington, NC (US); Janice Kimrey Anderson, Kure Beach, NC (US); Debra Kimrey Bowers, Albermarle, NC (US)

( * ) Notice: Subject to any disclaimer, the term of this patent is extended or adjusted under 35 U.S.C. 154(b) by 122 days.

(21) Appl. No.: 13/801,323

(22) Filed: Mar. 13, 2013

(65) Prior Publication Data

US 2014/0276524 A1    Sep. 18, 2014

(51) Int. Cl.
  *A61F 13/15* (2006.01)
  *A61F 13/64* (2006.01)
  *A61F 13/56* (2006.01)
  *A61F 13/62* (2006.01)

(52) U.S. Cl.
  CPC .............. *A61F 13/64* (2013.01); *A61F 13/565* (2013.01); *A61F 13/5622* (2013.01); *A61F 13/62* (2013.01); *A61F 2013/5683* (2013.01); *A61F 2013/5694* (2013.01)

(58) Field of Classification Search
  CPC ................ A61F 13/56; A61F 13/5622; A61F 2013/5683; A61F 2013/5694; A61F 13/62; A61F 13/64; A61F 13/496
  USPC .................................. 604/392, 396, 387, 391
  See application file for complete search history.

(56) References Cited

U.S. PATENT DOCUMENTS

| | | | |
|---|---|---|---|
| 2,564,094 A * | 8/1951 | Brandl | 604/392 |
| 3,995,638 A * | 12/1976 | Schaar | 604/389 |
| 3,999,548 A | 12/1976 | Hernandez | |
| 4,044,767 A | 8/1977 | Tritsch | |
| 4,985,025 A | 1/1991 | Lingertat et al. | |
| 4,988,346 A | 1/1991 | Pfefferkorn | |
| 5,135,522 A * | 8/1992 | Fahrenkrug et al. | 604/385.3 |
| 5,374,262 A | 12/1994 | Keuhn, Jr. et al. | |
| 5,806,096 A | 9/1998 | Pennington | |
| 6,197,011 B1 | 3/2001 | Freitas et al. | |
| 6,629,966 B2 | 10/2003 | Shimada et al. | |
| 7,008,410 B2 | 3/2006 | Gustin et al. | |
| 7,174,860 B2 | 2/2007 | Solomon | |
| 2002/0151863 A1 | 10/2002 | Toyoshima | |
| 2007/0293835 A1 | 12/2007 | Roehrl et al. | |
| 2008/0000005 A1 | 1/2008 | Rogerson et al. | |
| 2008/0086104 A1 | 4/2008 | Karlsson | |

FOREIGN PATENT DOCUMENTS

| | | |
|---|---|---|
| EP | 0 858 787 A1 | 8/1998 |
| EP | 1 495 742 B1 | 1/2005 |
| WO | WO 96/31177 | 10/1996 |

* cited by examiner

*Primary Examiner* — Jacqueline Stephens
(74) *Attorney, Agent, or Firm* — Christie, Parker & Hale, LLP

(57) ABSTRACT

An absorbent garment including a shell having a front panel and a rear panel, the front panel and the rear panel both having an exterior-facing surface and an interior-facing surface; a fastening system coupled to the shell, the fastening system including a waist strap having a first end portion and a second end portion configured such that the first end portion and the second end portion can be overlapped over the rear panel; and a buckle strap coupled to the exterior surface of the rear panel and configured to extend over the waist strap and to be attached to the interior surface of the rear panel.

10 Claims, 3 Drawing Sheets

REAR FASTENING ABSORBENT GARMENT

FIELD OF THE INVENTION

Embodiments of the present invention relate to a garment adapted to absorb bodily fluids and a fastening system for such a garment.

BACKGROUND OF THE INVENTION

Absorbent garments, such as diapers and incontinence guards, among others, are often worn by those who do not have sufficient control over their bodily fluid excretions. Such absorbent garments typically have a multilayered configuration including an outer liquid-impervious shell, an inner liquid permeable layer and an absorbent batt between the inner and outer layers. Additionally, the absorbent garment usually includes a fastening system to secure the garment in its proper position on the wearer. Although many variations of fastening system for absorbent garments are used, most fastening systems use at least one strap or band that can be fixed to the body of the garment by an adhesive. Further, most fastening systems are designed to be easily accessible for the wearer and for a caretaker and allow for relatively simple removal of the absorbent garment.

Often, a wearer of an absorbent garment is a young child, or an adult with diminished mental faculties, and therefore, the wearer may have a tendency to attempt to remove the absorbent garment even if it is not in the wearer's best interest to do so. Since the wearer typically requires the help of a caretaker, if the fastening system of the absorbent garment were slightly more difficult to remove for the wearer, yet still relatively easy for a caretaker to remove, the wearer would benefit and the caretaker's job would not be substantially more difficult.

SUMMARY

Embodiments of the present invention include an absorbent garment having a shell including a front panel and a rear panel, the front panel and the rear panel both having an exterior-facing surface and an interior-facing surface; and a fastening system coupled to the shell, the fastening system including a waist strap having a first end portion and a second end portion configured such that the first end portion and the second end portion can be overlapped over the rear panel; and a buckle strap coupled to the exterior surface of the rear panel and configured to extend over the waist strap and to be attached to the interior-facing surface of the rear panel.

In one embodiment, the absorbent garment further includes a loop attached to an interior-facing surface of the front panel, wherein the waist strap extends through the loop. In one embodiment, the waist strap is separable from the shell.

Additionally, in one embodiment, the absorbent garment also includes a fastening patch on an interior-facing surface of the rear panel and configured to couple the buckle strap to the shell. The fastening patch and the buckle strap may be made from the same material and the waist strap and the buckle strap may be made from the same material. In one embodiment, the rear panel has a pair of openings and wherein the waist strap extends through the pair of openings. Additionally, the buckle strap may be configured to traverse an edge of the shell.

In further embodiments, the waist strap may include a self-adhesive material and/or an elastic material.

DETAILED DESCRIPTION OF THE DRAWINGS

In general, embodiments of the present invention relate to a rear fastening absorbent garment that is relatively difficult to remove for the wearer, particularly for a wearer having limited dexterity, but relatively easy to remove for an attendant or caregiver. More specifically, one embodiment of the absorbent garment includes a fastening system including a waist strap having ends that can be overlapped over a rear panel of the garment and attached to each other. The fastening system also includes a buckle strap having a first end portion fixed to an exterior surface of the rear panel, the buckle strap able to extend portion over the overlapped end portions of the waist strap and fastened to an interior surface of the rear panel to secure the absorbent garment in a desired position on the wearer. Because the fastening system requires the wearer to reach around behind his or her back, unfasten the buckle strap attached to the interior surface of the absorbent garment and then unfasten the overlapped end portions of the waist strap, also located behind the wearer, the fastening system of the absorbent garment is relatively difficult to remove for the wearer, particularly for one with limited dexterity. However, because the straps are easily accessible by another person, the fastening system is relatively easy to be uncoupled or unfastened by a caretaker or an attendant.

Figure 1:
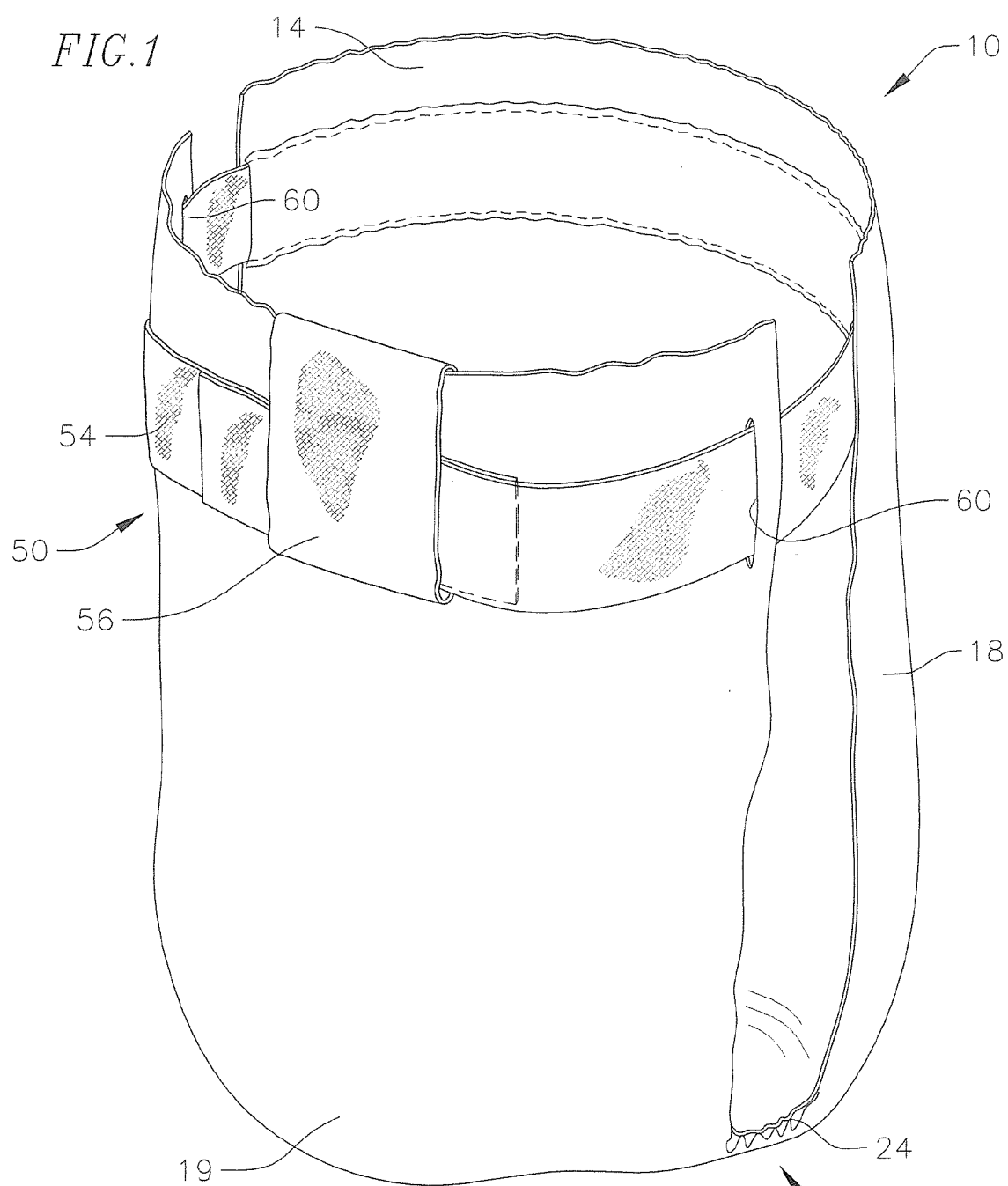
FIG. 1 is a perspective view of an absorbent garment according an embodiment of the present invention.
Figure 2:
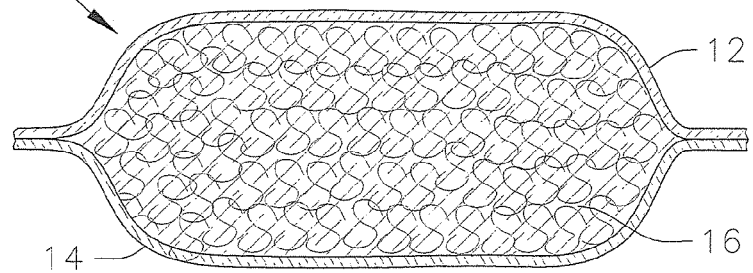
FIG. 2 is a cross-sectional view of a shell of the absorbent garment of FIG. 1.

With reference to FIGS. 1-2, an embodiment of a disposable absorbent garment 10 of the present invention is provided as an incontinence product for adults. However, it will be appreciated that the absorbent garment 10 could also be configured and sized for a child. The disposable absorbent garment 10 generally includes a shell 11 configured to be worn by a wearer and a fastening system 50 for keeping the absorbent garment on the wearer during an appropriate time and allowing for the removal of the absorbent garment when desired. As will be appreciated, the shell 11 is worn generally around the mid-section by the wearer, similar to underwear, and generally serves to absorb bodily secretions from the wearer who usually does not have sufficient control of his or her body to reliably reach a restroom. The shell 11 must be able to be secured to the wearer to keep it in place, but also should be easily removable so that it can be replaced when soiled. Additionally, the fastening system 50 may be integral with the shell 11 or may be at least partially removable, if not entirely removable, from the shell so that it can be reused, as described in more detail below.

As shown in FIG. 2, the shell 11 includes an outer layer 12, such as a substantially liquid impermeable backing sheet, that generally faces away from a wearer when the absorbent garment 10 is being worn, an inner layer 14, such as a substantially liquid permeable bodyside liner, that generally faces toward the wearer, and an absorbent core 16, such as an absorbent batt, located between the inner layer and the outer layer and configured to absorb fluid from the wearer. The outer layer 12 and the inner layer 14 are longer and wider than the absorbent core 16, so that the peripheries of the inner layer and the outer layer form margins that are sealed together using, for example, ultrasonic bonding, adhesive, or another similar fastener. In one embodiment, the inner layer 12 and the outer layer 14 are substantially the same size and thus, both extend along a full length of the absorbent garment 10.

However, it will be appreciated that the inner layer 14 may be a smaller size than the outer layer 12, and therefore the outer layer may form the exterior layer of the absorbent garment 10 facing both away from and toward the wearer in some places, generally near the waist portion of the garment.

With reference again also to FIG. 1, the shell 11 is generally rectangular and includes a front panel 18 and an opposite rear panel 19. As will be appreciated, the shell 11 may be one integral piece or separate pieces connected together, but the front and rear panels 18, 19 are designated as such for descriptive purposes to better illustrate embodiments of the present invention. Generally, the front panel 18 is adjacent to the front of the wearer's body and the rear panel 19 is adjacent to the back of a wearer's body. A crotch section 22 is located between the front panel 18 and the rear panel 20 and includes the outer layer 12, the inner layer 14 and the absorbent core 16. Although the shell is described as being generally rectangular, it may also be T-shaped, I-shaped, hourglass-shaped or irregularly shaped without departing from the spirit and scope of the present invention.

In one embodiment, the front panel 18 and the rear panel 19 can be attached together to form a ready-to-wear garment that can be pulled up on the wearer like a pair of shorts. Alternatively, the shell 11 can be a "flat shell," wherein the front panel and the rear panel are not attached together in the waist area before the wearer puts on the garment, but rather are configured to be coupled together after being placed on the wearer by, for example, inserting a waist strap through waist strap openings 60 in the rear panel, as described below.

The shell 11 may also include elastic strands 24 longitudinally oriented along each side margin of the garment 10 and attached to the outer layer 12, the inner layer 14 or both. The elastic strands 24 are located primarily in the crotch section 22 and extend toward the front panel 18 and the rear panel 20. The elastic strands assist in holding the shell 22 against the body and also form seals around the leg of the wear to substantially prevent leakage of fluid from the garment 10.

The fastening system 50 according to an embodiment of the present invention includes two straps, namely, a waist strap 54 and a buckle strap 56, that are used together to secure and hold the absorbent garment 10 in position on a wearer and also to make it relatively difficult for the wearer to uncouple the fastening system, particularly accidentally, and to thereby remove the garment.

Figure 3:
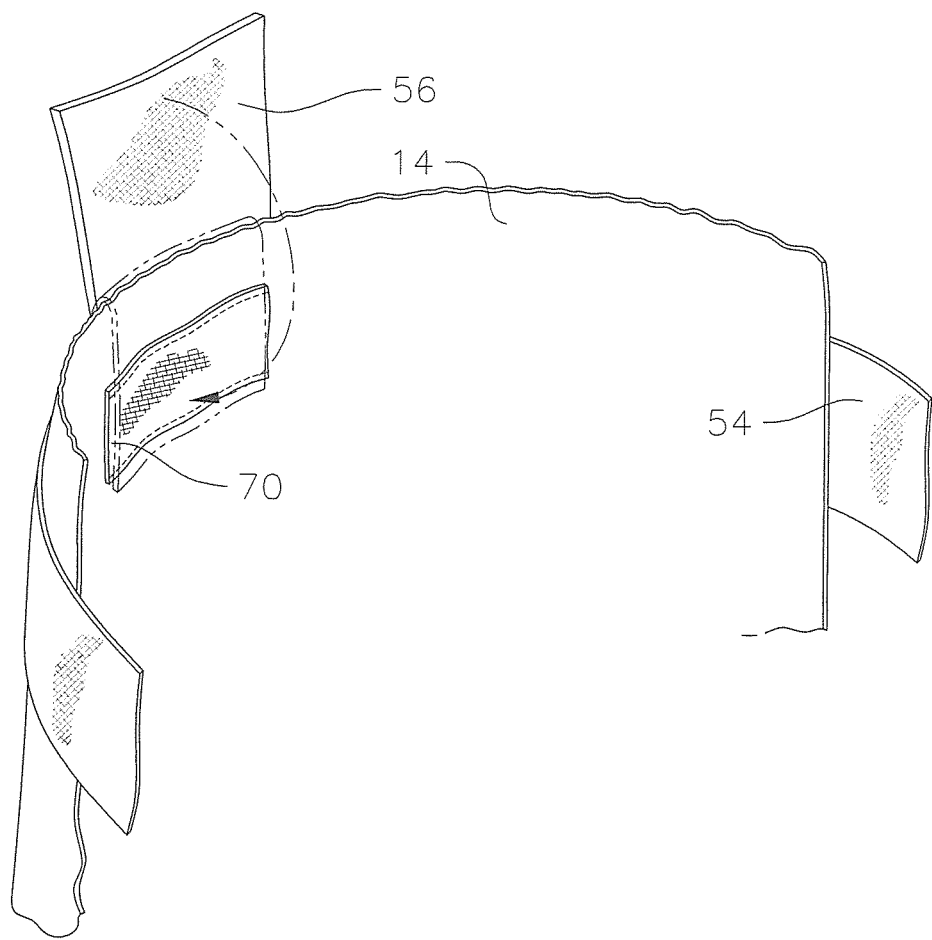
FIG. 3 is a partial perspective view of a rear panel of the absorbent garment of FIG. 1.

With reference now also to FIG. 3, the waist strap 54 is attached to the shell 11, and more specifically, attached adjacent to the inner layer 14 of the front panel 18 such that the strap will generally encircle the wearer's waist. The waist strap 54 may be made from a generally elastic material to allow the waist strap to stretch to accommodate differently sized wearers and also to apply pressure to secure the absorbent garment to the wearer. In one embodiment, the waist strap 54 may be made from a material that can attach to itself so that the waist strap 54 can act as a belt without the need for clips, an adhesive section, or other fastening devices, and also so that the waist strap can be unattached and reattached repeatedly. In one embodiment, the waist strap may be made from DOME® self grip, self-adhering athletic tape bandage.

Figure 4:
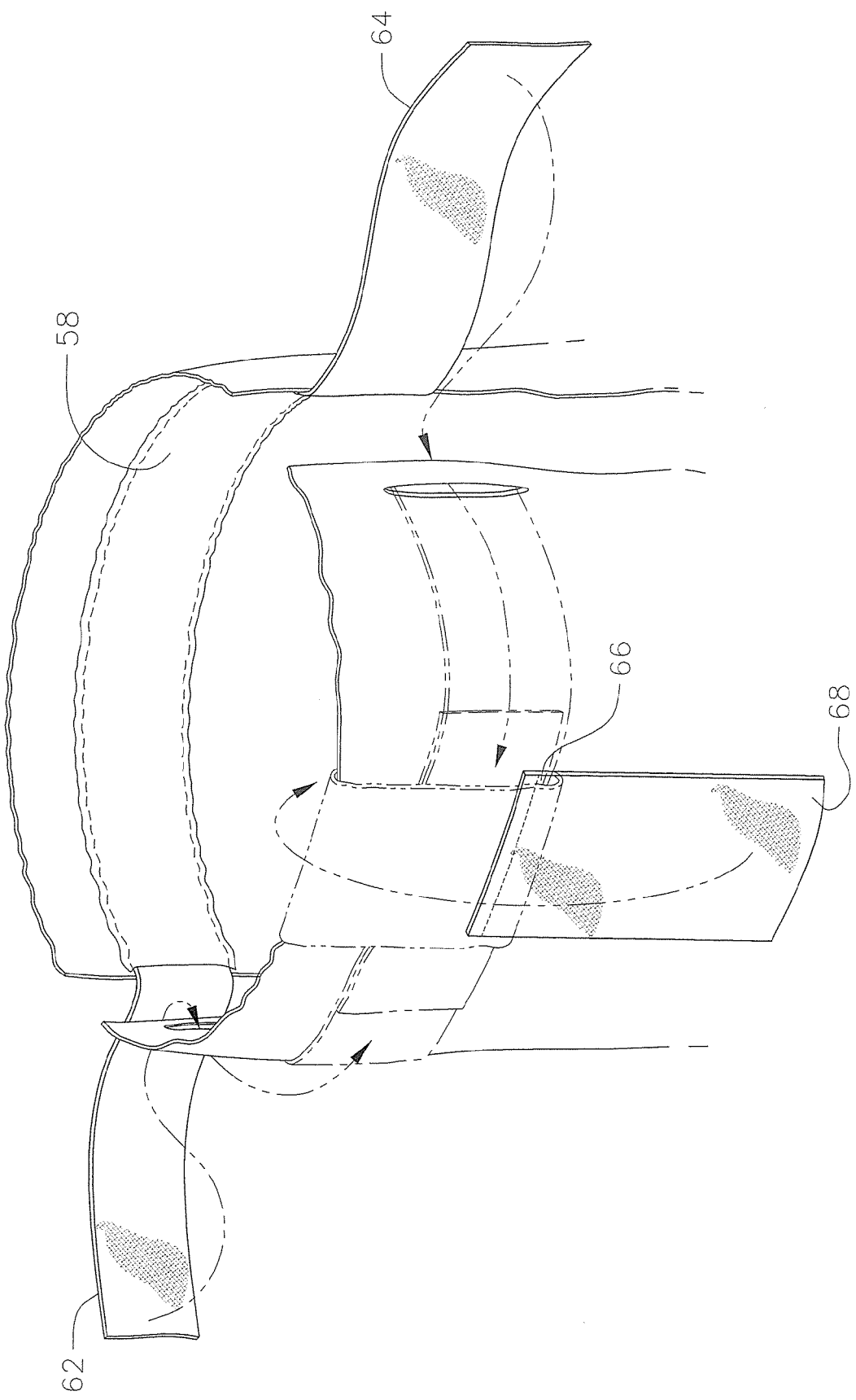
FIG. 4 is a rear view of a portion of the absorbent garment of FIG. 1.

In one embodiment a shown in FIG. 4, the waist strap 54 may be accommodated on the front panel 18 by a loop 58 formed by attaching fabric to the inner layer 14. More specifically, the fabric may be stitched or bonded along its edges to create the loop 58 through which the waist strap 54 can pass, allowing the waist strap 54 to be adjustable. Additionally, the loop 58 allows the waist strap to be removed and replaced by another waist strap or to be removed so that the waist strap can be reused once the original shell 11 has been soiled.

The shell 11 can include a single loop that extends substantially along an entire length of the inner layer 14 of the front panel 18. However, it will be appreciated that the shell 11 may have a plurality of loops, such as those used to hold a belt around the waist of a pair of pants. Alternatively, the waist strap 54 can be attached directly to the inner layer 12 or the outer layer 14 itself or may be incorporated between the inner and outer layers.

As noted above, the waist strap 54 extends from the front panel 18 and is positioned to generally encircle a wearer's waist. The waist strap 54 has a first end portion 62 and a second end portion 64 that extend freely from the shell 11. In one embodiment, each end portion 62, 64 of the waist strap 54 extends from a respective waist strap opening 60 in the rear panel 20 to couple the waist strap to the rear panel and to allow the waist strap to secure the shell 11 on the wearer. The waist strap 54 has a length such that when a wearer is wearing the absorbent garment, the first end portion 62 and the second end portion 64 can be overlapped and attached to each other over the rear panel 18.

The buckle strap 56 is configured and oriented to work in conjunction with the waist strap 54 as part of the fastening system 50. The buckle strap 56 has a fixed end portion 66 attached to the rear panel 20, more specifically, to the outer layer 12 of the rear panel, and a free end portion 68 that is configured to extend over an edge of the rear panel to be attached to the inner layer 14 of the rear panel. The fixed end portion 66 of the buckle strap 56 is attached to the outer layer 12 at a position such that when the free end portion 68 of the buckle strap is attached to the inner layer 14, as described in more detail below, the buckle strap can extend over the overlapping portions of the waist strap 54. In one embodiment, the buckle strap 56 is attached farther from the waist edge of the shell 11 than the waist strap 54 so that the buckle strap can cover a portion of the waist strap when it is attached to the inner layer 14 or to the interior surface of the shell 11.

In one embodiment, the buckle strap 56 is made from a generally elastic material that can be adhered to itself. For example, the buckle strap 56 can be made from DOME® self grip, self-adhering athletic tape bandage, and further, the waist strap 54 and the buckle strap 56 can be made from the same material. Alternatively, the fastening system 50 can be fastened by other fasteners, for example, an adhesive or a hook and loop configuration (i.e., VELCRO®).

A fastening patch 70 is fixed to the inner layer 14 of the rear panel 20 to allow the buckle strap 56 to be attached thereto. The fastening patch 70 may be made from a material that allows for the repeated attachment and disattachment of the buckle strap 56. In one embodiment, the fastening patch 70 is made from the same self-gripping material as the buckle strap 56, but it will be appreciated that it may be made from a different material. Additionally or alternatively, the buckle strap 56 can include an adhesive to allow for attachment and disattachment of the buckle strap.

The fastening patch 70 may be dimensioned to allow the buckle strap 56 to be sufficiently coupled to the fastening patch. As such, the fastening patch 70 may have a width substantially equal to or greater than a width of the buckle strap 56 and, in one embodiment, may have a length between about 0.5 and about 2 inches.

The fastening patch 70 is spaced from the waist edge of the rear panel 19 to ensure that the buckle strap 56 can be attached far enough from the edge to reduce the likelihood that the wearer will accidentally uncouple the buckle strap from the fastening patch 70. In one embodiment, the fastening patch 70 may be spaced from the waist edge of the rear panel 19 by about 0.5 inch. The fastening patch 70 may be affixed to the rear panel 20 by any appropriate fastening technique such as stitching, adhesive bonding or the like.

Use of the absorbent garment 10 will now be described. Initially, the absorbent garment 10 is put on by inserting the wearer's legs through the leg holes 26. Alternatively, for a "flat shell" absorbent garment where the front panel 18 is not attached to the rear panel 20, the garment can be placed on the wearer so that the crotch portion 22 is substantially aligned with the wearer's crotch, the front and rear panels 18, 20 can be folded upward, and then the first and second end portions 62, 64 of the waist strap 54 can be inserted through the openings 60 to couple the front and rear panels together.

Once the absorbent garment is at a desired location on the wearer, the first end portion 62 of the waist strap 54 is stretched in a first direction and the second end portion 64 of the waist strap is stretch in a second direction substantially opposite to the first direction so that the waist strap is snug against the wearer's body. Once the waist strap 54 is stretched to a desired amount, the first end portion 62 and the second end portion 64 can be overlapped and attached together to maintain the strap in place. As noted above, in one embodiment, the waist strap 54 is made from a material that allows it to be affixed to itself by pressure, and therefore the strap can be attached, detached and reattached repeatedly until a desired fit is obtained.

When the first and second end portions 62, 64 of the waist strap 54 have been attached together, the buckle strap 56 may then be extended over the end portions of the waist strap and over the waist edge of the rear panel 20. Then, the buckle strap 56 can be attached to the fastening patch 70 to be secured in place, effectively covering the overlapped end portions 62, 64 of the waist strap 54 and thereby making it more difficult for a wearer to unfasten the straps 54, 56 and take off the absorbent garment 10.

To remove the absorbent garment 10, the buckle strap 56 is uncoupled from the fastening patch 70 on the interior side of rear panel 20, located generally adjacent the wearer's lower back. When the buckle strap 56 has been uncoupled, the first and second ends 62, 64 of the waist strap 54 can then be uncoupled from each other to be loosened from the wearer's waist. The shell 11 can then be removed from the wearer. As noted above, if the waist strap 54 is not permanently fixed to the shell 11, the waist strap can be removed from the shell 11, if the shell is to be discarded, and saved to be used with another shell.

Although the absorbent garment according to exemplary embodiments of the present invention has been described for illustrative purposes, those skilled in the art will appreciate that various modifications are possible without departing from the scope and spirit of the invention as disclosed in the appended claims.

What is claimed is:

1. An absorbent garment comprising:
    a shell comprising a front panel and a rear panel, the front panel and the rear panel both having an exterior-facing surface and an interior-facing surface; and
    a fastening system coupled to the shell, the fastening system comprising:
        a waist strap having a first end portion and a second end portion configured such that the first end portion and the second end portion can be overlapped over the rear panel; and
        a buckle strap coupled to the exterior surface of the rear panel and configured to entirely extend over the waist strap and to be attached to the interior-facing surface of the rear panel.

2. The absorbent garment of claim 1, further comprising a loop attached to an interior-facing surface of the front panel, wherein the waist strap extends through the loop.

3. The absorbent garment of claim 1, wherein the waist strap is separable from the shell.

4. The absorbent garment of claim 1, further comprising a fastening patch on an interior-facing surface of the rear panel and configured to couple the buckle strap to the shell.

5. The absorbent garment of claim 4, wherein the fastening patch and the buckle strap comprise the same material.

6. The absorbent garment of claim 1, wherein the waist strap and the buckle strap comprise the same material.

7. The absorbent garment of claim 1, wherein the rear panel has a pair of openings and wherein the waist strap extends through the pair of openings.

8. The absorbent garment of claim 1, wherein the buckle strap is configured to traverse an edge of the shell.

9. The absorbent garment of claim 1, wherein the waist strap comprises a self-adhesive material.

10. The absorbent garment of claim 1, wherein the waist strap comprises an elastic material.

\* \* \* \* \*